United States Patent [19]

Kakizawa et al.

[11] Patent Number: 4,957,360
[45] Date of Patent: Sep. 18, 1990

[54] OPHTHALMIC DISEASE DETECTION APPARATUS

[75] Inventors: Koichiro Kakizawa, Okazaki; Tadashi Ichihashi, Hino, both of Japan

[73] Assignee: Kowa Company Ltd., Japan

[21] Appl. No.: 338,466

[22] Filed: Apr. 14, 1989

Related U.S. Application Data

[63] Continuation of Ser. No. 926,650, Nov. 3, 1986, abandoned.

[30] Foreign Application Priority Data

Nov. 21, 1985 [JP] Japan .................. 60-259772

[51] Int. Cl.⁵ .............................................. A61B 3/10
[52] U.S. Cl. .................... 351/221; 351/211; 351/214

[58] Field of Search ............... 351/205, 211, 221, 212, 351/214

[56] References Cited

U.S. PATENT DOCUMENTS 4,702,576 10/1987 Magnante .................. 351/221

Primary Examiner—Paul M. Dzierzynski
Attorney, Agent, or Firm—Bruce L. Adams; Van C. Wilks

[57] ABSTRACT

An apparatus for detecting ophthalmic diseases such as inflammation in the camera oculi of a patient's eye. A laser beam is focussed at a selected spot in the camera oculi of an eye, and the light scattered from the eye is photoelectrically detected and converted into an electrical signal which is subsequently used to determine the protein concentration essential to ophthalmic disease detection in the camera oculi of the patient's eye.

6 Claims, 2 Drawing Sheets

OPHTHALMIC DISEASE DETECTION APPARATUS

This is a continuation of application Ser. No. 926,650, now abandoned, filed Nov. 3, 1986.

BACKGROUND OF THE INVENTION

1. Field of the Invention

This invention relates to an apparatus for detecting ophthalmic diseases in the camera oculi of a patient's eye, and more particularly to an apparatus for detecting ophthalmic diseases in which laser light is irradiated via an optical system at one spot in the camera oculi of the patient's eye and the laser light scattered therefrom is analyzed to measure the protein concentration for ophthalmic disease detection in the camera oculi.

2. Description of the Prior Art

The camera oculi is comprised of the camera oculi anterior (anterior chamber) and the camera oculi posterior (posterior chamber). The camera oculi anterior is defined by a space surrounded by the rear surface of the cornea, a part of ciliary body, iris, and the front surface of the crystalline lens, while the camera oculi posterior is defined by a space surrounded by the rear surface of the iris, inner surface of the ciliary body, and front surface of the crystalline lens. The camera oculi is filled with transparent humor aqueous, which has chemical and physical characteristics different from lymphatic liquid and has a close relation with the metabolism of the cornea or crystalline lens. The humor aqueous contains proteins the amount of increases and which causes the camera oculi to be turbid when the eye becomes inflammed.

In this respect, the measurement of protein concentration in the camera oculi of the patient's eye is of great importance in determining whether the camera oculi is inflammed, that is, whether a blood-aqueous barrier exists or not.

To measure the protein concentration in the camera oculi, a slit lamp microscope is very often used to determine the turbidity by grading via naked eyes. This is, however, disadvantageous because the judgement depends upon the person who performs the measurement.

On the other hand, a photographic measuring method has been developed to make a quantitative measurement of the protein concentration. This method is, however, too complicated to analyze, thus very difficult to apply in a clinical examination.

SUMMARY OF THE INVENTION

It is therefore an object of the present invention to provide an apparatus for detecting ophthalmic diseases, which is capable of easily and precisely measuring the protein concentration in the camera oculi of a patient's eye.

In accordance with the present invention, the ophthalmic disease detection apparatus disclosed herein includes means for focussing a laser beam at a selected spot in the camera oculi of a patient's eye. The light which is scattered from the eye is photoelectrically detected and converted into an electrical signal which represents the intensity of the scattered laser beam in terms of the number of photons contained in the scattered laser beam. The number of photons is counted by counting means to measure the protein concentration in the camera oculi of the patient's eye.

This arrangement makes it possible to calculate the protein concentration in the camera oculi of the patient's eye quantitatively on the basis of the measurement of the scattered laser beam from the camera oculi, thus providing powerful and effective means for the ophthalmic disease detection, particularly for the detection of inflammation in the camera oculi of the eye.

BRIEF DESCRIPTION OF THE DRAWINGS

The objects and features of the present invention will become more apparent from a consideration of the following detailed description taken in conjunction with the accompanying drawings in which.

DETAILED DESCRIPTION OF THE PREFERRED EMBODIMENTS

Figure 1:
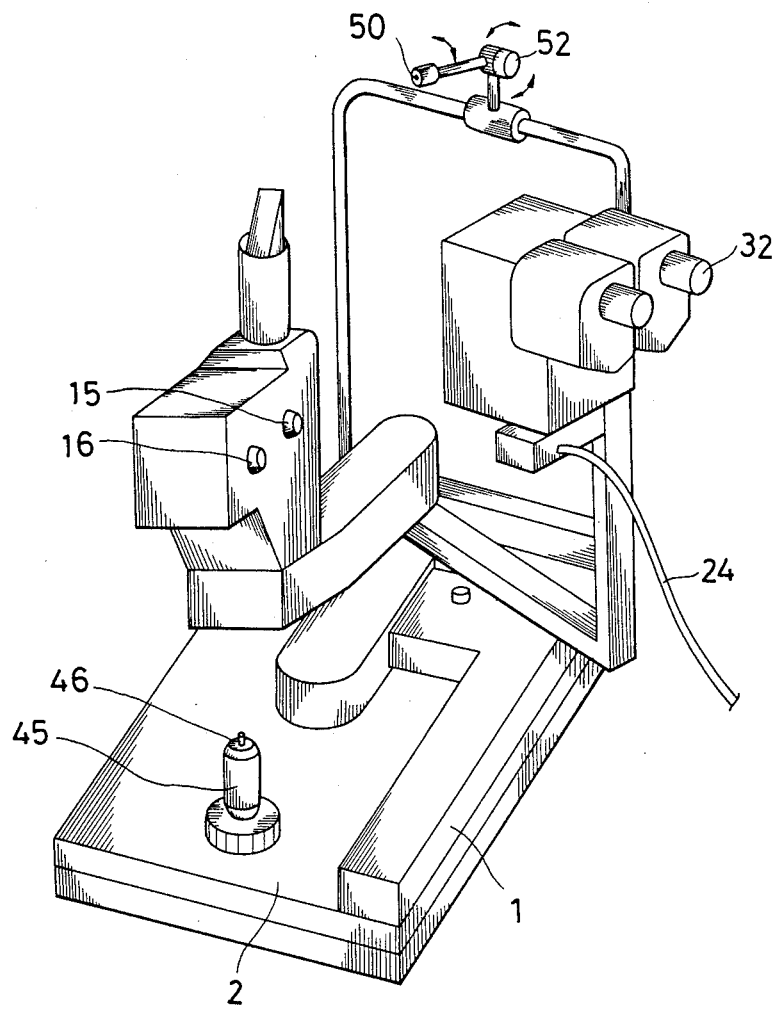
FIG. 1 is a schematic perspective view showing the whole appearance of the apparatus of the present invention.
Figure 2:
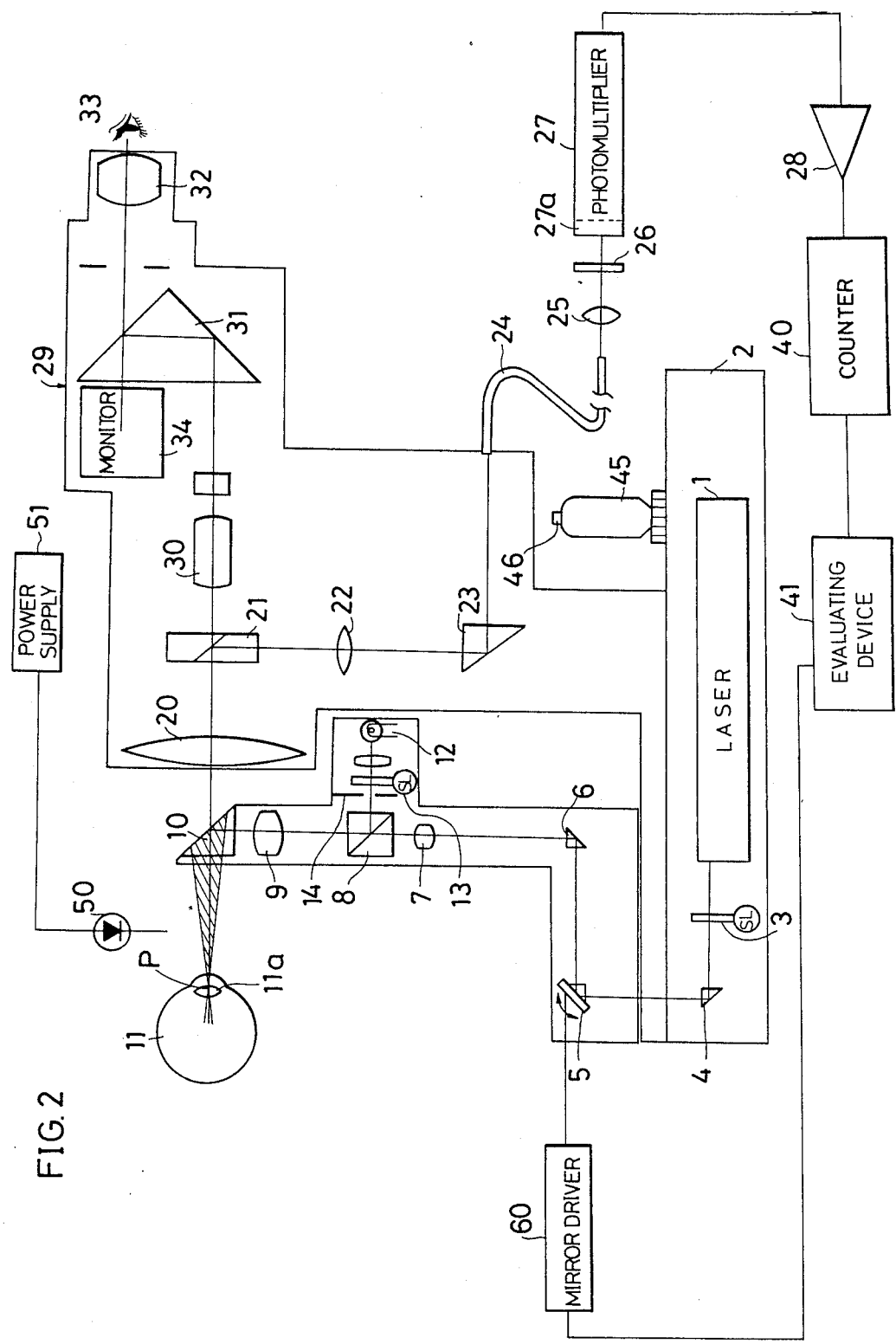
FIG. 2 is a block diagram showing the optical arrangement of the apparatus.

FIG. 1 and FIG. 2 show the general arrangement of an ophthalmic disease detection apparatus according to the present invention. In the drawings, reference numeral 1 indicates a helium-neon or argon type laser light source. The laser light source 1 is provided on a base 2. The light beam emitted from the laser light source 1 is passed through a laser filter 3, a prism 4, a pivotable mirror 5, a prism 6, a lens 7, a beam splitter 8, a lens 9, and a prism 10, and imaged so as to converge at one spot in a camera oculi 11a of patient's eye 11.

A slit light source 12 is provided in the laser emitting portion, and the light emitted from this slit light source 12 passes through a slit light shutter 13, a slit 14, and via the beam splitter 8, the lens 9 and the prism 10, whereupon the light emitted from the slit light source 12 is imaged as a slit image on the camera oculi 11a. Because the light beam emitted from the above mentioned laser light source 1 is imaged as a spot of light, the slit light image is intended to illuminate the periphery of the light spot and to thereby make the verification of the location of the spot image easy.

Adjustment as well as switching of the length of the slit along the lengthwise dimension of the slit 14 is carried out by means of an adjusting knob 15 and a switching knob 16, respectively.

Part of the laser light scattered from the spot being measured in the camera oculi 11a passes through the objective lens 20 of a detector 29, and is then divided by a beam splitter 21. A divided portion of the light passes through a lens 22, a prism 23, an optical fiber 24, a lens 25, and a shutter 26, and strikes a photomultiplier 27 which performs the function of a photoelectric converter. Another portion of the scattered light divided by the beam splitter 21 is directed in another direction and passes through a variator lens 30, a prism 31, and a monitoring plate 34. The image can be observed by an examiner 33 through an eyepiece 32.

The output signal of the photomultiplier 27 is amplified by an amplifier 28 and then applied to a counter 40 for counting the number of photons, thus determining the intensity of the scattered light detected by the photomultiplier 27. The counter 40 counts the number of electric pulses produced by the photoelectric converter 27. When the photomultiplier 27 receives the scattered light greater in intensity than a predetermined value, the counter 40 produces an output signal, which is then applied to an evaluating device 41 to calculate the protein concentration in the camera oculi 11a.

In the present invention, an eye fixation lamp 50 comprising a light emitting diode fed by a power supply 51 is disposed in such a position as to enable the patient to fix the gaze of his eye thereto. The tone of light emitted by the eye fixation lamp 50 is selected so as to differ from the tone of light emitted by the laser light source 1. Far example, if the light emitted from the laser light source is red, the light emitted by the eye fixation lamp 50 may be green. This eye fixation lamp 50 may be swivelled in the directions indicated by the arrows according to a linkage 52, and hence is adjustable to the optimal position for an individual patient.

An input device such as, for example, a joy stick 45 equipped with a push-button 46 is provided on the base 2, the manipulating of which effects the insertion of the laser filter 3, the slit light shutter 13, and the shutter 26 into the optical system, as well as the extraction of same therefrom.

The operation of an apparatus with such an arrangement will be explained below. Immediately preceding measurement, the light source 12 is turned on, and the slit image of the slit 14 is passed through the beam splitter 8, the prism 10 and the lens 9 and imaged on the camera oculi 11a over an area that covers the spot P to be measured. Next, light from the laser light source 1 is passed through the same optical arrangement and caused to converge on the spot to be measured.

The laser light beam is then scattered from the spot P, whereupon the beam splitter 21 directs a portion of the scattered light in the direction of the examiner 33 for observation, and simultaneously sends another portion thereof to the photomultiplier 27 via the optical system comprising the lens 22, the prism 23, and the optical fiber 24. The photomultiplier 27 detects the intensity of the scattered light scattered by the protein particles in the camera oculi 11a of the patient's eye. The counter 40 then counts the intensity of the scattered light in terms of the number of photons, and produces an output signal, which is applied to the evaluating device 41 in which the intensity of scattered light due to the scattering of big scattering particles such as cells is subtracted to derive therefrom the protein concentration due to the inflammation in the camera oculi of the patient's eye.

It is to be noted that the mirror 5 is constructed to be pivotable by a mirror driver 60 connected to the evaluating device 40 so as to be able to scan the laser light and displace the laser spot. This allows the displacement of the measuring spot to cover a greater area ,thus improving the accuracy in measuring the protein concentration.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

We claim:

1. An apparatus for detecting ophthalmic diseases in the camera oculi of a patient's eye which contains protein due to inflammation, comprising:
    a laser source for producing a laser beam;
    means for focussing the laser beam at a selected spot in the camera oculi of the patient's eye such that the focussed laser beam is scattered by the protein in the camera oculi during a predetermined measurement interval and including means for scanning the laser beam to displace the selected spot within the camera oculi during said measurement interval;
    photoelectric converting means for receiving the light scattered from the camera oculia and operative to convert the scattered light into corresponding electric pulses when the intensity of the received scattered light is greater than a predetermined value;
    counting means for counting the number of electric pulses produced by the photoelectric converting means to thereby measure the intensity of the scattered light; and
    means for calculating the protein concentration due to the inflammation in the camera oculi of the eye according to the measured intensity of the scattered light.

2. An apparatus according to claim 1; wherein the photoelectric converting means comprises a photomultiplier.

3. An apparatus for determining the concentration of protein particles in a patient's eye comprising: means for projecting a laser beam at a selected spot in a patient's eye; deflecting means for deflecting the laser beam during a measurement interval to scan the laser beam across an area in the patient's eye which includes the selected spot so that laser beam light is scattered by protein particles in the patient's eye; photoelectric converting means receptive of the scattered light for photoelectrically converting scattered light having an intensity greater than a predetermined value into electrical pulses the number of which corresponds to the intensity of the scattered light; counting means for counting the number of electrical pulses and producing a count value indicative of the intensity of the scattered light; and means receptive of the count value for determining therefrom the concentration of protein particles in the patient's eye.

4. An apparatus according to claim 3 wherein the photoelectric converting means comprises a photomultiplier.

5. An apparatus according to claim 3, wherein the means for determining the concentration of protein particles includes means for subtracting from the count value a value corresponding to light scattererd by particles other than protein particles in the patient's eye.

6. An apparatus according to claim 3, wherein the deflecting means includes means for periodically scanning the laser beam in at least one direction during the measurement interval.

* * * * *